(12) United States Patent
Mizutani et al.

(10) Patent No.: US 7,160,700 B2
(45) Date of Patent: Jan. 9, 2007

(54) GLYCOSYLTRANSFERASE GENES

(75) Inventors: Masako Mizutani, Kyoto (JP); Keiko Sakakibara, Wako (JP); Yoshikazu Tanaka, Otsu (JP); Takaaki Kusumi, Suita (JP); Eiichiro Ono, Otsu (JP)

(73) Assignee: International Flower Developments Proprietary Limited, Victoria (AU)

( * ) Notice: Subject to any disclaimer, the term of this patent is extended or adjusted under 35 U.S.C. 154(b) by 432 days.

(21) Appl. No.: 10/048,866

(22) PCT Filed: Jun. 1, 2001

(86) PCT No.: PCT/JP01/04675

§ 371 (c)(1),
(2), (4) Date: Apr. 24, 2002

(87) PCT Pub. No.: WO2001/092509

PCT Pub. Date: Dec. 6, 2004

(65) Prior Publication Data

US 2005/0003476 A1    Jan. 6, 2005

(30) Foreign Application Priority Data

Jun. 2, 2000    (JP)    ............................ 2000-170436

(51) Int. Cl.
*C12N 9/10* (2006.01)
*C12N 15/00* (2006.01)
*C12N 1/20* (2006.01)
*C07H 21/04* (2006.01)
*C12Q 1/48* (2006.01)

(52) U.S. Cl. .................... 435/75; 536/23.2; 435/320.1; 435/252.33; 435/254.2; 435/69.2; 435/15; 435/252.3; 435/325; 435/193

(58) Field of Classification Search ................ 435/193, 435/410, 252.3, 320.1, 69.1, 254.2, 252.33, 435/419, 254.1, 348, 325; 536/23.2; 530/350
See application file for complete search history.

(56) References Cited

FOREIGN PATENT DOCUMENTS

EP    967283 A1    12/1999

WO    WO 99/05287    2/1999

OTHER PUBLICATIONS

Fukuchi-Mizutani, M. et al., "Biochemical and Molecular Characterization of a Novel UDP-Glucose:Anthocyanin 3'-O-Glucosyltransferase, a Key Enzyme for Blue Anthocyanin Biosynthesis, from Gentian", *Plant Physiology* 132(3): 1652-1663, (2003).

Winkel-Shirley, B. et al., "Flavonoid Biosynthesis. A Colorful Model for Genetics, Biochemistry, Cell Biology, and Biotechnology", *Plant Physiology* 126(2): 485-493, (2001).

Markham, K. R., "Novel Anthocyanins Produced in Petals of Genetically Transformed Lisianthus", Phytochemistry 42(4): 1035-1038, (1996).

Horvath, D. M., et al., "Identification of an immediate-early salicylic acid-inducible tobacco gene and characterization of induction by other compounds", *Plant Molecular Biology* 31: 1061-1072, (1996).

Yoshida, K., et al., "Contribution of each caffeoyl residue of the pigment molecule of gentiodephin to blue color development", *Phytochemistry* 54: 85-92, (2000).

Tanaka, Y., et al., "Molecular and Biochemical Characterization of Three Anthocyanin Synthetic Enzymes from *Gentiana triflora*", *Plant Cell Physiol*, 37(5): 711-716, (1996).

Mato, Masami, et al., "Isolation and Characterization of a cDNA Clone of UDP-Galactose: Flavonoid 3-O-Galactosyltransferase (UF3GaT) Expresed in *Vigna mungo* Seedlings", *Plant Cell Physiol*. 39(11): 1145-1155, (1998).

Miller, K. D., et al., "Purification, Cloning, and Heterologous Expression of a Catalytically Efficient Flavonal 3-O-Galactosyltransferase Expressed in the Male Gametophyte of *Petunia hybrida*", *The Journal of Biological Chemistry* 274(48): 34011-34019, (1999).

*Primary Examiner*—Rebecca E. Prouty
*Assistant Examiner*—Malgorzata A. Walicka
(74) *Attorney, Agent, or Firm*—Scully, Scott, Murphy & Presser, P.C.

(57) ABSTRACT

A nucleic acid encoding a protein which has an amino acid sequence according to SEQ ID NO: 2, 12, or 14, or the amino acid sequence modified by addition or deletion of one or more amino acids and/or substitution by other amino acids, and which has activity to transfer a glycosyl group to the 3'-position of anthocyanins.

7 Claims, No Drawings

GLYCOSYLTRANSFERASE GENES

FIELD OF THE INVENTION

The present invention relates to nucleic acids encoding a protein which has an activity to transfer a glycosyl group to the 3'-position of anthocyanins, and to a method of using same.

BACKGROUND ART

In the floriculture industry, it is important to develop new and different varieties of flowering plants. In particular, regarding flower colour, which is one of the most important characteristics of flowering plants, classical breeding techniques that relies on crossing have been used to develop new varieties exhibiting various colours. However, since genetic resources are very limited among a particular plant species in which crossing can be carried out, it is rare for a single plant species to have a full spectrum of colour varieties.

Flower colour is predominantly due to a class of compounds, generally called anthocyanins, which belong to flavonoids. It has been known that there are various anthocyanins in plants, and the molecular structures of many of these compounds have already been determined. The colour of an anthocyanin is determined mainly by its structures (Harborne (1986) The Flavonoids, p. 565). Research has been conducted on enzymes, and genes encoding these enzymes, involved in biosynthesis of anthocyanins. There are some examples in which structure of anthocyanins were modified to alter flower colours by molecular biological techniques, and introduction of genes in plants (Holton et al. (1995) Plant Cell, 7, p. 1071; Tanaka et al. (1998) Plant Cell Physiol. 39. p. 1119).

The biochemical pathway for biosynthesis of anthocyanins up to anthocyanidin 3-glucosides is common in most flowering plants (Holton et al. (1995) Plant Cell, 7, p. 1071). Thereafter, anthocyanidin 3-glucosides present in plants are subjected to diverse modifications in a species- or varieties-specific manner. The diversity of this modification is one of the reason for the diversity of flower colours.

It is known that, although anthocyanins are unstable compounds in neutral solution, their stability is improved by modification with a glycosyl or an acyl group (Forkmann (1991) Plant Breeding, 106, p. 1). It is also known that they become bluer when an aromatic acyl group is added (Forkmann (1991) Plant Breeding, 106, p 1). It should be noted that the acyl group is not bound directly to the skeleton of the anthocyanidins, but indirectly via a glycosyl group that is bound to the anthocyanidin. Thus, in order for the stabilization and blue colour to be achieved by addition of the acyl group, it is necessary as a prerequisite that a glycosyl group have been added to the anthocyanidin.

In representative species of flowering plants exhibiting blue flower colour such as gentian, cineraria, and butterfly pea, their anthocyanins are modified with a glucose at the 3'-position of the B ring and the glucose is further modified with an aromatic acyl group (Yoshida et al. (1992) Tetrahedron, 48, p. 4313; Goto et al. (1984) Tetrahedron Letters, 25, p. 6021; Goto et al. (1991) Angrew. Chem. Int. Ed. Engl. 30, p. 17; respectively). Although it has been shown from a study using the main pigment of a gentian that the acyl group at the 3'-position of the B ring contributes to the stabilization and bluer colour of anthocyanidin (Yoshida et al. (2000) Phytochemistry 54, p. 85), it is prerequisite on the condition that a glycosyl group have been added to the 3'-position.

Several studies have been reported on glycosylation of flavonoids. For example, nucleic acids encoding enzymes that ctalyze a reaction to transfer a glucose molecule to a hydroxyl group at the 3-position of anthocyanidins have been cloned from snapdragon, gentian, perilla, barley, and corn (e.g. Tanaka et al. (1996) Plant Cell Physiol., 37, p. 711). Also, nucleic acids encoding enzymes that catalyze a reaction to transfer glactose to a hydroxyl group at the 3-position of anthocyanidins have been cloned from *vigna mungo*, and *petunia* (Mato et al. (1998) Plant Cell Physiol. 39, p. 1145; Miller et al. (1999) J. Biol. Chem. 273, p. 34011).

Nucleic acids encoding enzymes that catalyze a reaction to transfer glucose to a hydroxyl group at 5-position of anthocyanins have been cloned from perilla, verbena, and torenia (WO99/05287). A nucleic acid encoding enzymes that catalyze a reaction to transfer rhamnose to anthocyanidin 3-glucoside has been cloned from *petunia* (Brugliera et al. (1994) Plant J. 5, p. 81).

Also, a nucleic acid encoding enzymes that catalyze a reaction to transfer glucose to a hydroxyl group at the 7-position of flavonoids has been cloned from *Scutellaria baicalensis*, and it has been reported that a protein obtained by expressing this gene in *Escherichia coli* also catalyzes a reaction to transfer glucose to a hydroxyl group at the 7-position of flavonoids (Suzuki et al. (2000) Plant 210, p. 1006). A nucleic acid encoding enzymes that catalyze a reaction to transfer glucose to a hydroxyl group at the 5-position of betanidine has been cloned, and a protein obtained by expressing this gene in *Escherichia coli* catalyzes a reaction to transfer glucose to a hydroxyl group at the 4'- and 7-positions of flavonoids (Vogt et al. (1999) Plant J. 19:509–519).

However, there has been no report on nucleic acid encoding enzymes that catalyze a reaction to transfer a glucose to the 3'-position of anthocyanins, and activity of such a enzyme has not been measured. No such enzyme has been purified, nor has any nucleic acid encoding such an enzyme ever been cloned. Glycosyltransferase may catalyze reactions of transferring glucose to plural hydroxy groups, as described above. However, in order to accumulate a target anthocyanin in a plant, it is necessary to use an enzyme exhibiting high substrate-specificity.

DISCLOSURE OF THE INVENTION

According to the present invention, there is provided an isolated nucleic acid encoding a protein which has an activity to transfer a glycosyl group to a hydroxyl group at the 3'-position of anthocyanins, preferably transferring a glucose only to a hydroxyl group at the 3'-position of anthocyanins. By using the nucleic acid according to the present invention that encodes a protein having an activity to transfer a glycosyl group to a hydroxyl group at the 3'-position of anthocyanins, it is possible to alter the colour of flowers or stabilize an anthocyanin. The nucleic acid according to the present invention that encodes a protein having an activity to transfer a glycosyl group to a hydroxyl group at the 3'-position of anthocyanins is effective for stabilizing the anthocyanins as well as for altering the colour of flowers by controlling addition of a glycosyl-acyl group to the 3'-position of the anthocyanins.

As described above, although it became evident that flower colour can be altered by modification of anthocyanins using a protein which has an activity to transfer a glycosyl group to a hydroxyl group at the 3'-position of an anthocyanin, the property of this enzyme has not been characterized, and the enzyme has not been purified, nor has the nucleic acid encoding the enzyme been cloned. In the present invention, the activity of this enzyme has been discovered from the flower petals of gentian, and the protein having this activity has been purified from the flower petals of gentian.

By determining a partial amino acid sequence of the enzyme, nucleotide sequences encoding the amino acid sequences were assumed, and oligonucleotide primers with those sequences were synthesized. Based on the nucleotide primers, a nucleic acid encoding a protein which has an activity to transfer a glycosyl group to the 3'-position of anthocyanin was cloned from a cDNA library of the flower petal of gentian. By expressing a cloned nucleic acid in yeast cells, the enzyme activity to transfer a glycosyl group to the 3'-position of anthocyanins was confirmed. Thus, it was confirmed that the cloned nucleic acid encodes a protein having an activity to transfer a glycosyl group to the 3'-position of anthocyanins.

Further, the present inventor extracted RNA from flower petals of cineraria and from pea, constructed cDNA libraries, and screened them using the cDNA encoding the gentian glycosyltransferase described in Example 4 as a probe. It was found that the obtained clone encodes a protein having an activity to the transfer a glycosyl group to the 3'-position of anthocyanins.

Further, in the present invention, a transgenic plant was produced by introducing a gene encoding a glycosyltransferase to the 3'-position and a nucleic acid encoding a glycosyltransferase to the 5-position into *petunia*, and it was confirmed that these nucleic acids function successfully.

Thus, the present invention provides a nucleic acid encoding a protein which has an amino acid sequence shown by SEQ ID NO: 2, 12 or 14, and which has an activity to transfer a glycosyl group to the 3'-position of anthocyanins, or a nucleic acid encoding the above amino acid sequence modified with addition, deletion of one or more amino acids and/or substitution by other amino acids.

Also, the present invention provides a gene which encodes a protein having an activity to transfer a glycosyl group to the 3'-position of anthocyanins, and which is obtained by hybridization of a part or all of the nucleotide sequence encoding an amino acid sequence shown by SEQ ID NO: 2, 12 or 14 under the condition of 5×SSC, at 50° C.

The present invention also provides a vector comprising the above-described gene, and a host transformed with the above-described vector.

The present invention also provides the protein which is encoded by the above-described gene.

The present invention also provides a method for producing a protein having an activity to transfer a glycosyl group to the 3'-position of anthocyanins, comprising the steps of culturing or growing the above-described host, and extracting the protein having the activity.

The present invention further provides a transgenic plant having the above-described nucleic acid introduced, or offspring of the plant or plant tissue having the same property.

The present invention also provides a cut flower of the above-described plant or offspring thereof having the same property.

The present invention also provides a method for adding a glycosyl group to the 3'-position of anthocyanins using the above-described nucleic acid.

The present invention also provides a method for altering the colour of flowers by using the above-described nucleic acid.

PREFERRED EMBODIMENTS OF THE INVENTION

Nucleic acids as claimed in the present invention includes those encoding amino acid sequence as shown by SEQ ID NO: 2, 12 or 14. However, it is known that proteins having the amino acid sequence modified with addition or deletion of one or more amino acids and/or by substitution by other amino acids may continue to exhibit the same enzyme activity as the original protein. Therefore, a protein having an amino acid sequence shown by SEQ ID NO: 2, 12 or 14 modified with addition or deletion of one or more amino acids and/or substitution by other amino acids, and a nucleic acid encoding the protein, are also within the scope of the present invention as long as the protein continues to exhibit the same activity to transfer a glycosyl group to the 3'-position of anthocyanins.

The present invention relates to a nucleotide sequence shown by SEQ ID NO: 1, 11, or 13 or a nucleotide sequence encoding the amino acid sequences shown by SEQ ID NO: 2, 12 or 14, or a gene which encodes a protein having the activity to transfer a glycosyl group to the 3'-position of anthocyanins, and which hybridizes to a part of the above-described nucleotide sequence, for example the nucleotide sequence encoding six or more amino acids in the commonly conserved region among glycosyltransferases under the condition of, e.g., 5×SSC and 50° C. The appropriate hybridization temperature varies according to the nucleotide sequence or the length of the nucleotide sequence, and is preferably 50° C. or lower when using a DNA fragment of 18 bases encoding 6 amino acids as a probe.

Nucleic acids by such a hybridization may include naturally-occurring nucleic acids including, but not limited to, those derived from plants, for example, nucleic acids derived from cineraria, butterfly pea, lobelia, California lilac. The nucleic acid selected by hybridization may be a cDNA or a genome DNA.

The present invention also relates to the use of a nucleic acid for altering the colour of flowers wherein the nucleic acid encodes a protein having an amino acid sequence exhibiting homology of about 20% or more, preferably 50% or more, for example 60% or 70% or more, with an amino acid sequence shown by SEQ ID NO: 2, 12 or 14, and having an activity to transfer a glycosyl group to the 3'-position of anthocyanins.

As specifically shown in Examples, a nucleic acid having a native nucleotide sequence can be obtained, for example, by screening of a cDNA library. A DNA encoding an enzyme which has a modified amino acid sequence can be synthesized on the basis of DNA having a native nucleotide sequence using ordinary site-specific mutagenesis or the PCR method. For example, a DNA fragment to which a modification is to be introduced is obtained by treatment of the native cDNA or genome DNA with restriction enzymes. Then, using this fragment as a template, and using a primer having the desired modification introduced, site-specific mutagenesis or the PCR method is carried out to obtain DNA fragments having the desired modification introduced therein. Thereafter, the DNA fragment having the desired modification introduced therein may be ligated to a DNA fragment encoding other parts of the target enzyme.

Alternatively, in order to obtain DNA encoding an enzyme which has a shortened amino acid sequence, DNA encoding an amino acid sequence longer than the target amino acid sequence, such as the DNA encoding the full-length amino acid sequence, may be cut with suitable restriction enzymes. If the resulting DNA fragment does not encode the entire target amino acid sequence, a DNA fragment consisting of the missing sequence may be synthesized and ligated.

By expressing the obtained nucleic acid using the nucleic acid expression system in *Escherichia coli* and yeast, and by measuring the enzyme activity, it is possible to confirm that the obtained nucleic acid encodes a protein having an activity to transfer a glycosyl group to the 3'-position of anthocyanins. It is also possible by expressing the nucleic acid to obtain, as a gene product, a protein having an activity to transfer a glycosyl group to the 3'-position of anthocyanins by using an antibody to an amino acid sequence shown by SEQ ID NO: 2, 12 or 14. Further, it is possible to use an antibody to clone a nucleic acid encoding a protein having an enzyme activity to transfer a glycosyl group to the 3'-position of anthocyanins derived from other living organisms.

Therefore, the present invention relates to a recombination vector, especially an expression vector, comprising the above-described nucleic acid, and to a host transformed by the vector. Both prokaryote and eukaryote may be used as a host. In prokaryote, bacteria such as *Escherichia coli* that belongs to the genus *Escherichia*, or *Bacillus subtilis* that belongs to the genus *Bacillus* may be used as a usual host. As a eukaryotic host, a lower eukaryote, for example, a eukaryotic micro-organism such as yeast and mold fungi which belong to fungi may be used.

In yeast, a micro-organism belonging to *Saccharomyces* genus such as *Saccharomyces cerevisiae* or the like may be used as a host. In mold fungi, a micro-organism belonging to the genus *Aspergillus* such as *Aspergillus oryzae*, *Aspergillus niger*, and a micro-organism belonging to the genus *Penicillium*, may be used as hosts. Animal cells and plant cells may also be used as hosts. In animal cells, cell system derived from a mouse, hamster, monkey, a human, etc. may be used. Insect cells such as silkworm cells, or even an adult silkworm itself, may be used as a host.

The expression vector of the present invention includes expression control region that depends upon the kind of host to which it is to be introduced, such as a promotor and a terminator, replication origin, and the like. As a promotor for an expression vector in bacteria, commonly used promoters such as a trc promotor, tac promotor, lac promotor or the like may be used. As a promotor for a expression vector in yeast, a glyceraldehyde-3-phosphate dehydrogenase promotor, PH05 promoter or the like, and as a promotor for an expression vector in mold fungi, an amylase promotor, a trpC promotor or the like may be used.

As a promotor for an expression vector in animal cell hosts, a viral promotor such as SV 40 early promotor, SV 40 late promotor, or the like may be used. Construction of the expression vector may be performed in accordance with any of the usual methods known to those skilled in the art, using restriction enzymes, ligases, etc. Transformation of host cells with the expression vector may also be performed in accordance with any of the usual methods.

The target protein can be obtained by culturing, raising or growing the host transformed with the above-described expression vector, and by recovering the gene product from the culture or the like, and purifying in accordance with usual methods, for example filtration, centrifuging, crushing of cells, gel filtration chromatography, ion exchange chromatography, and the like.

Although nucleic acids encoding enzymes having activity to transfer a glycosyl group to 3'-position of anthycyanins derived from gentian, cineraria, and butterfly pea, are described herein, the present invention is not restricted to these nucleic acids, and the origin of the nucleic acid encoding a protein which has an activity to transfer a glycosyl group to the 3'-position of anthocyanins may be a plant, an animal, or a micro-organism. Irrespective of the origin, the nucleic acid can be utilized for altering flower colour as long as the protein has an activity to transfer a glycosyl group to the 3'-position of anthocyanins.

Further, the present invention relates to a transgenic plant or its offspring or tissue thereof, including cut flowers, which is obtained by introducing a nucleic acid encoding a protein having an activity to transfer a glycosyl group to the 3'-position of anthocyanins and which has its hue thereby adjusted. By using a nucleic acid obtained according to the present invention which encodes a protein having an activity to transfer a glycosyl group to the 3'-position of anthocyanins, it is possible to enhance glycosylation of the 3'-position of anthocyanins, or to suppress glycosylation of the 3'-position of anthocyanins, and consequently to alter the colour of flowers. Here, in conjunction with the above-described nucleic acid, a nucleic acid encoding an enzyme having activity to transfer an acyl group to the glucose at the 3'-position may be used.

In the present state of the art, it is possible to introduce a nucleic acid into a plant and to cause the nucleic acid to be expressed in a constructive or tissue-specific fashion. It is also possible to suppress the expression of a target nucleic acid using, for example, an anti-sense method or a co-suppression method.

Examples of plants that can be transformed in this manner include, but not limited to, roses, chrysanthemums, carnations, snapdragons, cyclamens, orchids, prairie gentians, freesias, gerberas, gladiolus, baby's breath, kalanchoes, lilies, pelargoniums, geraniums, petunias, torenias, tulips, rice, barley, wheat, rapeseed, potatos, tomatos, poplars, bananas, eucalyptuses, sweet potatos, soybeans, alfalfa, lupine, corn, and cauliflower.

EXAMPLE

The present invention will be described in detail below in accordance with Examples thereof. Unless otherwise specified, the molecular biological techniques employed are those set forth in WO96/25500.

Example 1

Measurement of Enzyme Activity to Transfer a Glycosyl Group to the 3'-position of Anthocyanin in Gentian Flower Petals A crude enzyme solution was extracted from gentian flower petals in accordance with the procedure already reported procedure (Fujiwara, Plant Cell Engineering Series 9(1998), p. 99, Syujyunsha Co.).

20 µl of the crude enzyme extract solution, 10 µl of 0.5M potassium phosphate (pH 8.5), 10 µl of 5 mM UDP-glucose, 10 µl of delphinidin 3,5-diglucoside (1.5 mg/ml) were mixed and maintained at 30° C. for 10 minutes. Then, following the procedure of Fujiwara et al. (Fujiwara et al. Plant J. (1998)), reaction was terminated, and the reaction product was analyzed using high performance liquid chromatography (HPLC). As a result, it was determined that gentian flower petals contain an enzyme having activity to transfer a glycosyl group to the 3'-position of an anthocyanin.

Example 2

Purification of a Enzyme having an Activity to Transfer a Glycosyl Group to the 3'-position of Anthocyanins The method employed for purifying an enzyme is, unless otherwise specified, that already reported procedure (Fujiwara, Plant Cell Engineering Series 9(1998), p. 99, Syujyunsha Co.). A crude extract solution was obtained from about 500 g of gentian flower petals, and a fraction of 40 to 70% saturation was obtained by salting out using ammonium sulfate. After dissolving this fraction in buffer A (20 mM Tris-HCl (pH 7.5), 10% glycerol, 10 μM p-amidinophenylmethanesulfonyl fluoride (APMSF), 0.1% beta-mercaptoethanol), product was desalted using Sephadex G-25 (Pharmacia Co.). The desalted fraction was adsorbed to Q-Sepharose (Pharmacia Co.) equilibrated with the buffer A, and eluted with a linear gradient formed with buffer A and buffer A containing 500 mM NaCl.

The active fraction was adsorbed to Blue A (Amicon Co.) equilibrated with the buffer A, and was eluted with a linear gradient formed with the buffer A and the buffer A containing 1.5 M NaCl. The active fraction was dialyzed in Buffer B (20 mM sodium phosphate pH 7.0, 10% glycerol, 10 μM p-amidinophenylmethanesulfonyl fluoride (APMSF), 0.1% beta-mercaptoethanol), and then adsorbed to DEAE-Sepharose (Pharmacia Co.) equilibrated with the buffer B, and eluted with a linear gradient formed with the buffer B and the buffer B containing 500 mM NaCl. The active fraction was concentrated and desalted with Microcon 30 (Amicon Co.), and after the solvent was replaced by 0.5 ml of the buffer B, protein was purified using Superose 12 (Pharmacia Co.) equilibrated with the buffer B. Using the above-described method, approximately 7.5 μg of a purified protein was obtained.

Example 3

Determination of Partial Amino Acid Sequence of the Enzyme Having Activity to Transfer a Glycosyl Group to the 3'-position of Anthocyanins Using the purified protein obtained in Example 2, its partial amino acid sequences were determined in accordance with the method of Fujiwara et al. (Fujiwara et al. Plant J. (1998)). The amino acid sequences obtained are as set forth below.

```
GT15 Lys-Ser-Gln-Val-Pro-Pro           (SEQ ID NO: 3)

GT25 Asn-Ile-Ser-Glu-Ser-Glu-Asn-Asp   (SEQ ID NO: 4)

GT27 Ala-Val-Glu-Glu-Gly-Ser-Ser-      (SEQ ID NO: 5)
Tyr-Ser-Asp-Leu-Ser-Ala

GT32 Glu-His-Arg-Pro-Gln-Ala-Leu-      (SEQ ID NO: 6)
Val-Ala-Asp-Leu-Phe-Phe-Tyr-Trp-Ala-
Asn-Asp-Ala-Ala

GT42 Gly-Trp-Ala-Pro-Gln-Val-Leu-      (SEQ ID NO: 7)
Ile-Leu-Glu-His-Glu-Ala-Val-Gly-Ala-
Phe-Val
```

From among above sequences, based on the sequence Trp-Ala-Asn-Asp-Ala-Ala (SEQ ID NO: 8), an oligonucleotide G3'GT2 was constructed.

G3'GT2  5'-TGGGCIAA(T/C)GA(T/C)GCIGC-3'  (I: inosine) (SEQ ID NO: 9)

XhoI-T (5'-CTCGAGTTTTTTTTTTTTTTTTT-3') (SEQ ID NO: 10) was also synthesized.

Example 4

Cloning of the Nucleic Acid Encoding an Enzyme to Transfer a Glycosyl Group to the 3'-position of Anthocyanins Using 3 μl of phage solution of gentian petal cDNA library as a template, and 50 pmole of each of G3'GT2 and XhoI-T as primers, and using Taq polymerase (Takara), PCR reaction was carried out in total volume of 50 μl following the method recommended by the manufacturer. After the solution was maintained at 95° C. for 2 minutes, the reaction was carried out for 25 cycles with a cycle profile consisting of 95° C. for 1 minute, 42° C. for 2 minutes and 72° C. for 3 minutes, and then the solution was maintained at 72° C. for 10 minutes.

The reaction solution was separated using agarose gel electrophoresis, and a band of approximately 700 bp was recovered and was subcloned to pCRII vector (Clonetech) in accordance with the method recommended by the manufacturer. The nucleotide sequence of the obtained plasmid was determined, and it was found that the plasmid contained nucleotide sequences encoding the amino acid sequences of GT15 and GT25. Screening of gentian cDNA library was performed using this DNA as a probe, and clones containing full-length cDNA were obtained. The complete nucleotide sequence of one clone (pG3'GT7) was determined and is shown in SEQ ID NO: 1. The amino acid sequence deduced from this nucleotide sequence is shown in SEQ ID NO: 2.

Example 5

Expression of a Nucleic Acid Encoding a Protein Which has Activity to Transfer a Glycosyl Group to the 3'-position of Anthocyanins in Yeast A DNA fragment of approximately 1.6 kbp, which was obtained by digestion of pG3'GT7 with XhoI, was recovered. This DNA was ligated to a DNA fragment obtained by digesting pYE22m with SalI, and the obtained plasmid that has the initiation codon nearer to the promotor on pYE22m was denoted by pYG3'GT7. pYE22m was constructed according to the method as set forth in Japanese Patent Publication No. 4-228078. This plasmid was introduced into yeast cells to obtain transformed yeast cells. After the yeast cells were cultured and disrupted with glass beads, enzyme activity was measured as in Example 1 using delphinidin 3,5-diglucoside as substrate. It was found that the extract from transformed yeast exhibits the activity to transfer a glycosyl group to the 3'-position of anthocyanins.

No activity was found in the yeast in which the plasmid was not introduced. When cyanidin 3,5-diglucoside was used as substrate, no new peak was produced. Thus, the enzyme exhibits activity to the delphinidin 3,5-diglucoside which has 3 hydroxyl groups in the B ring, but exhibits no activity for adding a glycosyl group to cyanidin 3,5-diglucoside which has only 2 hydroxyl groups, suggesting that this enzyme has high specificity to the structure of the B ring of the substrate, and has activity for adding a glycosyl group specifically to the third hydroxyl group in the B ring.

Example 6

Expression of a Nucleic Acid Encoding a Protein Which has an Activity to Transfer a Glycosyl Group to the 3'-position of Anthocyanins in *Escherichia coli*

Using the PCR method, an NcoI site was introduced so as to coincide with the initiation methionine codon of pG3'GT7, and the region from the initiation methionine to poly A of pG3'GT7 was inserted in the NcoI/KpnI site of *E. coli* expression vector pQE61 (QIAGEN). The obtained *E. coli* expression vector was denoted by pG3'Q1. pG3'Q1 was introduced into the *Escherichia coli* JM105 strain, and after preculturing overnight at 37° C., a part of the precultured medium was innoculated into 8 L of a main culture medium, and was cultured at 27° C. until $OD_{600}$=0.6. To induce expression of the 3'GT gene, IPTG was added so as to reach a final concentration of 0.4 mM, and was cultured overnight at 27° C. After cells were collected, washed, and suspended in 400 ml of crushing buffer (25 mM Tris-HCl (pH 7.5), 250 mM NaCl, 1 mM EDTA, 0.5% β-mercaptoethanol), the cells were disrupted by ultrasonic treatment. After centrifuging, the resultant supernatant was subjected to processing with DE52, and a 40–70% ammonium sulfate precipitate fraction was recovered. After desalting, the crude protein solution was loaded onto a DEAE-TOYOPEARL (Toso Co.) pre-equilibrated with buffer C (25 mM Tris-HCl (pH 7.5), 0.5% β-mercaptoethanol), and was eluted with buffer C containing 0–0.5 M NaCl. The active fraction was recovered, adsorbed to BlueA (Amicon Co.) equilibrated buffer C, and was eluted with a linear gradient formed with the buffer C and the buffer C containing 2 M NaCl. The obtained active fraction was used in the reaction, to be described later, as a purified sample of the 3'GT portion.

Example 7

Confirmation of the Position of Glycosyl Addition

Using the purified sample of the 3'GT portion obtained in Example 6, the reaction was conducted at a scale 100 times larger than that described in Example 1 delphinidin 3,5-diglucoside as substrate. After the reaction was incubated at 30° C. for 15 minutes, 1 M HCl was added to a final concentration of 0.16 M, to stop the reaction. After the reaction solution was loaded onto Seppak C18 (manufactured by Waters Co.) and rinsed for desalting and for removal of protein, the pigment fraction was eluted with a solution of 50% acetonitrile and 0.1% TFA, and concentrated under reduced pressure. The pigment fraction was purified using separation HPLC. The preparative HPLC equipped with a column YMC-Pack D-ODS-5 (manufactured by YMC Co.) of 2 cmφ*25 cm, and mobile phase of A: water, B: 50% acetonitrile 0.5% TFA, 6 ml/min., linear gradient of B20%→B50% (60 min), and detection was performed with A520 nm⁻AUFS:0.32. The eluted product was collected in 20~22 minutes, was concentrated under reduced pressure, and was then freeze-dried. LC-Q (Thermoquest Co.) was used as MS, and measurement was conducted with ESI, positive. As a result, a peak of molecular ion 789 (M+) was obtained, and it was confirmed that the reaction product is delphinidin 3,5'-diglucoside modified by addition of a glucose.

Also, 2.5 mg of the freeze-dried compound was subjected to NMR analysis. Using 0.6 ml of 10% TFA-d/CD30D as a measurement solvent, measurement of $^1H$ NMR and ROESY ($^{13}C$ NMR) was conducted by DMX-500. As a result of ROESY, ROE was observed between the peak of the 2'-position of the B ring at 8.12 ppm and the peak of the 1-position of glucose at 5.03 ppm. From this result, it was apparent that the binding positions of the three glucoses are the 3-, 5-, and 3'-positions of delphinidin, and it was confirmed that the product of the enzyme reaction is delphinidin 3,5,3'-triglucoside, as was intended.

Example 8

Analysis of Substrate Specificity

Using the purified sample of the 3'GT portion obtained in Example 6, the substrate-specificity of the 3'GT was analyzed. It was confirmed as in Example 5 that 3'GT exhibits activity to delphinidin 3,5-diglucoside which has three hydroxyl groups in the B ring, but not to cyanidin 3,5-diglucoside which has only two hydroxyl groups. It also exhibits activity to delphinidin 3-glucosyl-5-caffeoylglucoside. Assuming the relative activity to delphinidin 3,5-glucoside to be 100%, the activity to delphinidin 3-glucosyl-5-caffeoylglucoside is about 50%. Trace amount of products (1% or less) were also observed using delphinidin or delphinidin 3-diglucoside as a substrate. From retention time of HPLC and the absorption spectrum, the reaction product is considered to be a substrate having a glycosyl group added to the 3'-position thereof.

Example 9

Expression in *Petunia* of a Nucleic Acid Encoding a Protein Which has Activity to Transfer a Glycosyl Group to the 3'-position of Anthocyanin A *petunia* (Skr4 X Da strain) cannot add a rhamnose to a glucose at the 3-position due to a mutation of the gene encoding anthocyanin 3-rhamnosyl transferase, and accumulates delphinidin 3-glucoside as the main anthocyanin pigment of flower petals. A binary vector pSPB1112 was constructed for coexpression of a pG3'GT7 cDNA which encodes a protein having activity to transfer a glycosyl group to the 3'-position of anthocyanin of gentian and a pTGT5 cDNA (WO99/05287) which encodes a protein having an activity to transfer a glycosyl group to the 5-position of anthocyanin derived from torenia, and was introduced into the *petunia*.

Construction of pSPB1112 was performed as follows. First, an expression cassette comprising the E12 35S promotor having two repetitions of enhancer sequences on the upstream of the cauliflower mosaic virus 35S promotor (Mitsuhara et al. (1996) Plant Cell Physiol. 37, p. 49), gentian pG3'GT7 cDNA of and a NOS terminator was constructed on the plasmid vector pUC19 with a HindIII site at the 5' end, and a EcoRI site at the 3' end. This was cut out at HindIII/EcoRI, and was inserted into the HindIII/EcoRI cleavage sites of a binary vector pBINPLUS for introduction into plants (vanEngelen et al., Transgenic Research 4, p. 288) to produce pSPB1110. Meanwhile, a plasmid vector pUCAA was constructed with AscI inserted in both ends of a multi-cloning site of pUC19, and an expression cassette for torenia pTGT5 comprising a MAC1 promotor (Comai et al. (1990) Plant Mol. Biol. 15, p. 373), torenia pTGT5 cDNA, and a mannopine synthease gene terminator was constructed on PUCAA with the HindIII site at the 5' end, and the EcoRI site at the 3' end. The entire pTGT5 expression cassette was cut out from the pUCAA vector by AscI digestion, and was inserted in AscI cleavage sites of pSPB1110 described above in the same direction as the expression cassette of gentian pG3'GT7, i.e. both expression cassettes are oriented with LB upstream. The resultant plasmid was denoted by pSPB1112.

Plants that formed shoot on a selective medium containing kanamycin, and exhibited rooting were acclimatized. Anthocyanin pigment was extracted from flower petals of each transformed plant, and was analyzedusing HPLC. In all the transformed plants analyzed, 0.5~6.8% (relative to total anthocyanin) of delphinidin 3,5',3'-triglucoside was detected. On the other hand, in the extract of lower petals of best plant, no delphinidin 3, 5',3'-triglucoside was detected, and most of the pigment was delphinidin 3-glucoside. It was evident from this result that, in the transformed plants, the transformed nucleic acids encoding gentian 3'-glycosyl-transferanse and the torenia 5-glycosyltransferase successfully functioned, and produced delphinidin 3,5',3'-trigluco-side using delphinidin 3-glucoside as a substrate.

Example 10

Cloning of a Nucleic Acid Which Encodes a Protein Having an Activity to Transfer a Glycosyl Group to the 3'-position Derived from Cineraria Petals of cineraria contain cinerarin (delphinidin 3-malo-nyl-glucoside, 7-caffeoyl-glucosyl-caffeoyl-glucoside, 3'-caffeoyl-glucoside) as the main anthocyanin pigment. Thus, cineraria is expected to have a nucleic acid which encodes a protein having activity to transfer a glycosyl group to the 3'-position of anthocyanins. RNA was extracted from flower petals of cineraria by the method using guanidine hydrochloride buffer-ultracentrifuge (WO96/25500), and cDNA library was constructed. Using DIG labeling and the detection kit (Amersham) in accordance with the method recommended by the manufacturer, about 300,000 phage clone of the cDNA library of cineraria flower petal as screened using DIG-labelled gentian pG3'GT7 cDNA by the PCR method as a probe. Screening was conducted in accordance with the method recommended by the manufacturer of the above-mentioned kit, using a hybridization buffer containing 30% formamide. Hybridization was performed at 37° C., and washing was conducted in 5×SSC containing 1% SDS at 55° C. As a result of sequencing of 15 positive clones, 1 clone pSPB1090 was obtained which encodes an amino acid sequence exhibiting high identity with 3' GT of gentian. The entire nucleotide sequence of pSPB1090 CDNA is shown in SEQ ID NO: 11, and the amino acid sequence deduced from the nucleotide sequence is shown in SEQ ID NO: 12.

The protein encoded by pSPB1090 cDNA exhibited 39% identity at the level of amino acid with the 3'-glycosyltransferase encoded by gentian pG3'GT7 cDNA. On the other hand, the identity of the protein encoded by pSPB1090 with other glycosyltransferase, for example, 5-glycosyltransferase of anthocyanin of perilla, and 3-glycosyltransferase of anthocyanin of snapdragon or gentian, was all 24%. Since the glycosyltransferase encoded by cineraria pSPB1090 cDNA exhibited significantly higher identity with the gentian 3'-glycosyltransferase, it can be said that the glycosyl-transferase encoded by cineraria pSPB1090 cDNA has activity to transfer a glycosyl group to the 3'-position of anthocyanins.

Example 11

Cloning of Nucleic Acid Which Encodes a Protein Having an Activity to Transfer a Glycosyl Group to the 3'-position Derived from Butterfly Pea Petals of butterfly pea contain ternatin (delphinidin 3-ma-lonyl-glucoside, 3'-glucosyl-coumaroyl-glucosyl-couma-royl-glucoside, 5'-glucosyl-coumaroyl-glucosyl-coumaroyl-glucoside) as the main anthocyanin pigment. Thus, butterfly pea is expected to have a nucleic acid which encodes a protein having activity to transfer a glycosyl group to the 3'-position of anthocyanins. In the same manner as in Example 10, a cDNA library was constructed using RNA extracted from flower petals of butterfly pea to obtain a cDNA library for hybridization with DIG labeled gentian pG3' GT7 cDNA. Sequencing of 51 positive clones revealed that one clone encodes a protein with high identity with 3' glucosyltransferase of gentian. The entire nucleotide sequence of pSPB1087 cDNA that can be considered as a full length of cDNA is shown in SEQ ID NO: 13, and the amino acid sequence deduced from this nucleotide sequence is shown in SEQ ID NO: 14.

The protein encoded by pSPB1087 cDNA exhibits an identity of 53% at the level of amino acid with the gentian 3'-glycosyltransferase. This score of identity is significantly higher compared to that with other glycosyltransferase, for example, an identity of 28% with anthocyanin 5-glycosyl-transferase of perilla, or an identity of 25% with anthocya-nidine 3-glycosyltransferase of gentian. Identity of the protein encoded by cineraria pSPB1090 with the protein encoded by butterfly pea pSPB1087 was 44%. Also in the phylogenetic tree obtained by CLUSTAL W analysis (Nishimura, Oono, Protocol of Experiment on Protein 2, Structural Analysis (1997) Syujunsha), proteins encoded by pSPB1090 of cineraria and by pSPB1087 of butterfly pea are placed nearest to the 3-glycosyltransferase of anthocyanins.

From what has been described, it can be said that pSPB1090 of cineraria obtained in Example 10 and pSPB1087 of butterfly pea obtained in the present Example both encode proteins having activity to transfer a glycosyl group to the 3'-position of anthocyanins.

INDUSTRIAL APPLICABILITY

According to the present invention, a nucleic acid involved in biosynthesis of anthocyanins and encoding a protein which has activity to transfer a glycosyl group to the 3'-position of anthocyanins has been cloned for the first time. It is possible to express the nucleic acid encoding the protein at petal according to the present invention, or to suppress the expression, thereby to alter the structure of anthocyanins and the colour of flowers.

What is claimed is:

1. An isolated nucleic acid encoding a protein that has an activity to transfer a glycosyl group to the 3'-position of anthocyanins, wherein said nucleic acid comprises a nucleotide sequence selected from the group consisting of SEQ ID NO: 1, 11 and 13.

2. An isolated nucleic acid encoding a protein which has an activity to transfer a glycosyl group to the 3'-position of anthocyanins, and which comprises the amino acid sequence set forth in SEQ ID NO: 2, 12 or 14.

3. A vector comprising the nucleic acid according to claim 1 or 2.

4. An isolated host cell transformed with the vector of claim 3.

5. An isolated protein comprising the amino acid sequence set forth in SEQ ID NO: 2, 12 or 14.

6. A process for production of a protein comprising the steps of:
   culturing or growing the host according to claim 4; and
   collecting a protein having an activity to transfer a glycosyl group to the 3'-position of anthocyanins from the host.

7. A method for adding a glycosyl group to the 3' position of anthocyanins comprising expressing a nucleic acid according to claim 1 or claim 2 to produce a protein which transfers a glycosyl group to the 3'-position of anthocyanins, and contacting said protein with anthocyanins.

* * * * *

SEQUENCE LISTING

```
<160> NUMBER OF SEQ ID NOS: 14

<210> SEQ ID NO 1
<211> LENGTH: 1678
<212> TYPE: DNA
<213> ORGANISM: Gentiana triflora var. japonica
<220> FEATURE:
<221> NAME/KEY: CDS
<222> LOCATION: (30)..(1475)
```

<400> SEQUENCE: 1

```
attcattttg atcctcgagc ctagctttg atg gat cag ctt cac gtt ttc ttc      53
                                Met Asp Gln Leu His Val Phe Phe
                                 1               5 ttc cct ttc ttg gcc aat ggc cat atc ctt ccc acc ata gac atg gct     101
Phe Pro Phe Leu Ala Asn Gly His Ile Leu Pro Thr Ile Asp Met Ala
         10              15                  20 aaa tta ttc agc tcc cga gga gtt aag gca acc tta atc acc acc cac     149
Lys Leu Phe Ser Ser Arg Gly Val Lys Ala Thr Leu Ile Thr Thr His
 25              30                  35                  40 aac aac tcc gcc att ttc ctc aaa gct atc aac aga agc aaa atc ctg     197
Asn Asn Ser Ala Ile Phe Leu Lys Ala Ile Asn Arg Ser Lys Ile Leu
                 45                  50                  55 gga ttc gac ata tct gtt ctt aca atc aaa ttc cct tca gct gaa ttt     245
Gly Phe Asp Ile Ser Val Leu Thr Ile Lys Phe Pro Ser Ala Glu Phe
             60                  65                  70 ggt ttg cct gaa gga tac gag act gct gat caa gca aga tct ata gat     293
Gly Leu Pro Glu Gly Tyr Glu Thr Ala Asp Gln Ala Arg Ser Ile Asp
         75                  80                  85 atg atg gac gag ttt ttc aga gct tgt att ttg ctt caa gaa cct ctt     341
Met Met Asp Glu Phe Phe Arg Ala Cys Ile Leu Leu Gln Glu Pro Leu
 90                  95                 100 gag gag cta cta aaa gaa cat cgt cct caa gcc ctc gtc gcc gac ttg     389
Glu Glu Leu Leu Lys Glu His Arg Pro Gln Ala Leu Val Ala Asp Leu
105                 110                 115                 120 ttt ttc tac tgg gcc aac gac gct gca gct aaa ttt ggt atc cca aga     437
Phe Phe Tyr Trp Ala Asn Asp Ala Ala Ala Lys Phe Gly Ile Pro Arg
                125                 130                 135 ttg cta ttt cat ggg tca agt tct ttt gca atg att gct gca gag agt     485
Leu Leu Phe His Gly Ser Ser Ser Phe Ala Met Ile Ala Ala Glu Ser
            140                 145                 150 gtt agg cgc aat aaa cca tac aag aat ctt tcc tct gat tct gac cct     533
Val Arg Arg Asn Lys Pro Tyr Lys Asn Leu Ser Ser Asp Ser Asp Pro
        155                 160                 165 ttt gtg gtg cct gat att cct gat aaa atc ata ttg act aaa tca caa     581
Phe Val Val Pro Asp Ile Pro Asp Lys Ile Ile Leu Thr Lys Ser Gln
170                 175                 180 gtg cct acc ccg gat gaa aca gag gag aac aat aca cat att aca gag     629
Val Pro Thr Pro Asp Glu Thr Glu Glu Asn Asn Thr His Ile Thr Glu
185                 190                 195                 200 atg tgg aaa aac att tca gaa tcc gaa aat gat tgc tac gga gtt att     677
Met Trp Lys Asn Ile Ser Glu Ser Glu Asn Asp Cys Tyr Gly Val Ile
                205                 210                 215 gtt aac agt ttt tac gag ctg gag cct gat tat gtt gat tac tgc aaa     725
Val Asn Ser Phe Tyr Glu Leu Glu Pro Asp Tyr Val Asp Tyr Cys Lys
            220                 225                 230 aat gtt ttg gga aga aga gca tgg cat ata gga cct ctg tcg ctt tgt     773
Asn Val Leu Gly Arg Arg Ala Trp His Ile Gly Pro Leu Ser Leu Cys
        235                 240                 245 aac aat gaa ggt gaa gat gta gct gaa aga ggg aaa aaa tca gac att     821
Asn Asn Glu Gly Glu Asp Val Ala Glu Arg Gly Lys Lys Ser Asp Ile
250                 255                 260 gat gca cat gag tgt ctg aat tgg ctt gat tcc aag aac cca gat tca     869
Asp Ala His Glu Cys Leu Asn Trp Leu Asp Ser Lys Asn Pro Asp Ser
265                 270                 275                 280 gtt gtc tat gtt tgc ttt gga agc atg gct aac ttc aat gct gcc caa     917
Val Val Tyr Val Cys Phe Gly Ser Met Ala Asn Phe Asn Ala Ala Gln
                285                 290                 295
```

-continued

| | | |
|---|---|---|
| tta cat gaa ctt gca atg ggt ctt gaa gaa tcc gga caa gaa ttc atc<br>Leu His Glu Leu Ala Met Gly Leu Glu Glu Ser Gly Gln Glu Phe Ile<br>300                       305                  310 | 965 | |
| tgg gtt gta cga act tgt gtg gat gaa gaa gac gaa tca aaa tgg ttc<br>Trp Val Arg Thr Cys Val Asp Glu Glu Asp Glu Ser Lys Trp Phe<br>315                   320                  325 | 1013 | |
| cca gat gga ttt gaa aaa agg gtt caa gaa aac aat aag gga tta atc<br>Pro Asp Gly Phe Glu Lys Arg Val Gln Glu Asn Asn Lys Gly Leu Ile<br>330                   335               340 | 1061 | |
| ata aaa ggg tgg gca cct cag gtt cta att ctt gaa cat gaa gca gtt<br>Ile Lys Gly Trp Ala Pro Gln Val Leu Ile Leu Glu His Glu Ala Val<br>345                  350               355               360 | 1109 | |
| ggg gca ttt gtg agt cac tgc ggt tgg aat tca aca cta gag gga ata<br>Gly Ala Phe Val Ser His Cys Gly Trp Asn Ser Thr Leu Glu Gly Ile<br>365                 370                375 | 1157 | |
| tgc gga gga gta gcg atg gtg act tgg cca tta ttt gca gag caa ttt<br>Cys Gly Gly Val Ala Met Val Thr Trp Pro Leu Phe Ala Glu Gln Phe<br>380                  385                390 | 1205 | |
| tac aac gag aaa tta atg acg gat att ttg aga aca ggg gtt tct gtg<br>Tyr Asn Glu Lys Leu Met Thr Asp Ile Leu Arg Thr Gly Val Ser Val<br>395                  400                405 | 1253 | |
| ggt tcg ctg caa tgg agt aga gtg acg acg tcg gcg gtg gtt gtt aaa<br>Gly Ser Leu Gln Trp Ser Arg Val Thr Thr Ser Ala Val Val Val Lys<br>410                  415                420 | 1301 | |
| aga gaa tcc atc agc aaa gct gtc cgc cgc ctg atg gcg gag gaa gaa<br>Arg Glu Ser Ile Ser Lys Ala Val Arg Arg Leu Met Ala Glu Glu Glu<br>425                  430               435               440 | 1349 | |
| ggg gtc gac ata aga aac aga gca aaa gcc cta aag gaa aag gct aag<br>Gly Val Asp Ile Arg Asn Arg Ala Lys Ala Leu Lys Glu Lys Ala Lys<br>445                  450               455 | 1397 | |
| aag gca gtt gaa ggt ggt gga tcg tct tat tca gat ttg agt gct ctt<br>Lys Ala Val Glu Gly Gly Gly Ser Ser Tyr Ser Asp Leu Ser Ala Leu<br>460                  465               470 | 1445 | |
| tta gtc gaa tta agt tca tat cca cac aac taaaagatcg agaagtttta<br>Leu Val Glu Leu Ser Ser Tyr Pro His Asn<br>475                  480 | 1495 | |
| atatgctatc ttcacttaca tcgaattgat ggataataaa tctgaatcac tgatgccgga | 1555 | |
| ggcataacag aggataacgc aaggaataaa gtaagagaag aaaatcatag aaacagagat | 1615 | |
| aatactctga aatatattat tataataata tcaaattca actctaaaaa aaaaaaaaaa | 1675 | |
| aaa | 1678 | |

<210> SEQ ID NO 2
<211> LENGTH: 482
<212> TYPE: PRT
<213> ORGANISM: Gentiana triflora var. japonica

<400> SEQUENCE: 2

Met Asp Gln Leu His Val Phe Phe Pro Phe Leu Ala Asn Gly His
1               5                   10                  15

Ile Leu Pro Thr Ile Asp Met Ala Lys Leu Phe Ser Ser Arg Gly Val
            20                  25                  30

Lys Ala Thr Leu Ile Thr Thr His Asn Asn Ser Ala Ile Phe Leu Lys
        35                  40                  45

Ala Ile Asn Arg Ser Lys Ile Leu Gly Phe Asp Ile Ser Val Leu Thr
    50                  55                  60

Ile Lys Phe Pro Ser Ala Glu Phe Gly Leu Pro Glu Gly Tyr Glu Thr
65                  70                  75                  80

```
Ala Asp Gln Ala Arg Ser Ile Asp Met Met Asp Glu Phe Phe Arg Ala
                85                  90                  95
Cys Ile Leu Leu Gln Glu Pro Leu Glu Leu Leu Lys Glu His Arg
            100                 105                 110
Pro Gln Ala Leu Val Ala Asp Leu Phe Phe Tyr Trp Ala Asn Asp Ala
            115                 120                 125
Ala Ala Lys Phe Gly Ile Pro Arg Leu Leu Phe His Gly Ser Ser Ser
    130                 135                 140
Phe Ala Met Ile Ala Ala Glu Ser Val Arg Arg Asn Lys Pro Tyr Lys
145                 150                 155                 160
Asn Leu Ser Ser Asp Ser Asp Pro Phe Val Pro Asp Ile Pro Asp
                165                 170                 175
Lys Ile Ile Leu Thr Lys Ser Gln Val Pro Thr Pro Asp Glu Thr Glu
                180                 185                 190
Glu Asn Asn Thr His Ile Thr Glu Met Trp Lys Asn Ile Ser Glu Ser
                195                 200                 205
Glu Asn Asp Cys Tyr Gly Val Ile Val Asn Ser Phe Tyr Glu Leu Glu
    210                 215                 220
Pro Asp Tyr Val Asp Tyr Cys Lys Asn Val Leu Gly Arg Arg Ala Trp
225                 230                 235                 240
His Ile Gly Pro Leu Ser Leu Cys Asn Asn Glu Gly Glu Asp Val Ala
                245                 250                 255
Glu Arg Gly Lys Lys Ser Asp Ile Asp Ala His Glu Cys Leu Asn Trp
            260                 265                 270
Leu Asp Ser Lys Asn Pro Asp Ser Val Val Tyr Val Cys Phe Gly Ser
        275                 280                 285
Met Ala Asn Phe Asn Ala Ala Gln Leu His Glu Leu Ala Met Gly Leu
    290                 295                 300
Glu Glu Ser Gly Gln Glu Phe Ile Trp Val Val Arg Thr Cys Val Asp
305                 310                 315                 320
Glu Glu Asp Glu Ser Lys Trp Phe Pro Asp Gly Phe Glu Lys Arg Val
                325                 330                 335
Gln Glu Asn Asn Lys Gly Leu Ile Ile Lys Gly Trp Ala Pro Gln Val
                340                 345                 350
Leu Ile Leu Glu His Glu Ala Val Gly Ala Phe Val Ser His Cys Gly
                355                 360                 365
Trp Asn Ser Thr Leu Glu Gly Ile Cys Gly Gly Val Ala Met Val Thr
370                 375                 380
Trp Pro Leu Phe Ala Glu Gln Phe Tyr Asn Glu Lys Leu Met Thr Asp
385                 390                 395                 400
Ile Leu Arg Thr Gly Val Ser Val Gly Ser Leu Gln Trp Ser Arg Val
                405                 410                 415
Thr Thr Ser Ala Val Val Lys Arg Glu Ser Ile Ser Lys Ala Val
                420                 425                 430
Arg Arg Leu Met Ala Glu Glu Gly Val Asp Ile Arg Asn Arg Ala
    435                 440                 445
Lys Ala Leu Lys Glu Lys Ala Lys Ala Val Glu Gly Gly Gly Ser
        450                 455                 460
Ser Tyr Ser Asp Leu Ser Ala Leu Leu Val Glu Leu Ser Ser Tyr Pro
465                 470                 475                 480
His Asn

<210> SEQ ID NO 3
```

```
<211> LENGTH: 6
<212> TYPE: PRT
<213> ORGANISM: Artificial sequence
<220> FEATURE:
<223> OTHER INFORMATION: Description of Artificial Sequence: Amino
      acid sequence of a fragment  of an enzyme transferring a glycoside
      to 3'-pos

<400> SEQUENCE: 3

Lys Ser Gln Val Pro Pro
 1               5

<210> SEQ ID NO 4
<211> LENGTH: 8
<212> TYPE: PRT
<213> ORGANISM: Artificial sequence
<220> FEATURE:
<223> OTHER INFORMATION: Description of Artificial Sequence:Amino acid
      sequence of a fragment of    an enzyme transferring a glycoside
      to 3'-position of anthocyanins

<400> SEQUENCE: 4

Asn Ile Ser Glu Ser Glu Asn Asp
 1               5

<210> SEQ ID NO 5
<211> LENGTH: 13
<212> TYPE: PRT
<213> ORGANISM: Artificial sequence
<220> FEATURE:
<223> OTHER INFORMATION: Description of Artificial Sequence:Amino acid
      sequence of a fragment of an enzyme transferring a glycoside to
      3'-position of anthocyanins

<400> SEQUENCE: 5

Ala Val Glu Glu Gly Ser Ser Tyr Ser Asp Leu Ser Ala
 1               5                  10

<210> SEQ ID NO 6
<211> LENGTH: 20
<212> TYPE: PRT
<213> ORGANISM: Artificial sequence
<220> FEATURE:
<223> OTHER INFORMATION: Description of Artificial Sequence:Amino acid
      sequence of a fragment of an enzyme transferring a glycoside to
      3'-position of anthocyanins

<400> SEQUENCE: 6

Glu His Arg Pro Gln Ala Leu Val Ala Asp Leu Phe Phe Tyr Trp Ala
 1               5                  10                  15

Asn Asp Ala Ala
            20

<210> SEQ ID NO 7
<211> LENGTH: 18
<212> TYPE: PRT
<213> ORGANISM: Artificial sequence
<220> FEATURE:
<223> OTHER INFORMATION: Description of Artificial Sequence:Amino acid
      sequence of a fragment of an enzyme transferring a glycoside
      to 3'-position of anthocyanins

<400> SEQUENCE: 7

Gly Trp Ala Pro Gln Val Leu Ile Leu Glu His Glu Ala Val Gly Ala
 1               5                  10                  15

Phe Val
```

```
<210> SEQ ID NO 8
<211> LENGTH: 6
<212> TYPE: PRT
<213> ORGANISM: Artificial sequence
<220> FEATURE:
<223> OTHER INFORMATION: Description of Artificial Sequence:Amino acid
      sequence used as a basic of designing a primer

<400> SEQUENCE: 8

Trp Ala Asn Asp Ala Ala
 1               5

<210> SEQ ID NO 9
<211> LENGTH: 17
<212> TYPE: DNA
<213> ORGANISM: Artificial sequence
<220> FEATURE:
<223> OTHER INFORMATION: Description of Artificial Sequence:Primer
<220> FEATURE:
<221> NAME/KEY: misc_feature
<222> LOCATION: (6)
<223> OTHER INFORMATION: n=inosine
<220> FEATURE:
<221> NAME/KEY: misc_feature
<222> LOCATION: (15)
<223> OTHER INFORMATION: n=inosine

<400> SEQUENCE: 9
tgggcnaayg aygcngc                                                  17

<210> SEQ ID NO 10
<211> LENGTH: 23
<212> TYPE: DNA
<213> ORGANISM: Artificial sequence
<220> FEATURE:
<223> OTHER INFORMATION: Description of Artificial Sequence:Primer

<400> SEQUENCE: 10
ctcgagtttt tttttttttt ttt                                           23

<210> SEQ ID NO 11
<211> LENGTH: 1566
<212> TYPE: DNA
<213> ORGANISM: Senesio cruentus
<220> FEATURE:
<221> NAME/KEY: CDS
<222> LOCATION: (52)..(1406)

<400> SEQUENCE: 11
ggcacgagga aacctcaaca tatttctcta gaaatctaga atcaccaac a atg gca      57
                                                      Met Ala
                                                        1 att gac aaa ctt cac ttc ctt ttg gta ccc cac ata ggc cct ggc cac    105
Ile Asp Lys Leu His Phe Leu Leu Val Pro His Ile Gly Pro Gly His
     5                  10                  15 act att ccc atg ata gac atg gcc aaa ctc ctt tca aaa caa ccc aat    153
Thr Ile Pro Met Ile Asp Met Ala Lys Leu Leu Ser Lys Gln Pro Asn
 20                  25                  30 gtt gct atg gtc act ata gct acc acg cca ctc aat gtc atc cga tac    201
Val Ala Met Val Thr Ile Ala Thr Thr Pro Leu Asn Val Ile Arg Tyr
 35                  40                  45                  50 ggt cca act ctt gct gga ttg atc aaa acc aga ttc cta gag ctc cca    249
Gly Pro Thr Leu Ala Gly Leu Ile Lys Thr Arg Phe Leu Glu Leu Pro
                 55                  60                  65 ttt ccg gca gcc gag gtt gga tta cct gaa gga tgt gaa agc aca gat    297
Asn Pro Ala Ala Glu Val Gly Leu Pro Glu Gly Cys Glu Ser Thr Asp
             70                  75                  80
```

-continued

| | |
|---|---|
| aaa ctc cct agt cta gat ttt gtc cca aac ttt tta gct gct att gaa<br>Lys Leu Pro Ser Leu Asp Asn Val Pro Asn Asn Leu Ala Ala Ile Glu<br>            85                  90                  95 | 345 |
| atg cta caa caa aaa ctt gaa gag cgt ttt ggt acg tta aat cct cgt<br>Met Leu Gln Gln Lys Leu Glu Glu Arg Asn Gly Thr Leu Asn Pro Arg<br>100                 105                 110 | 393 |
| ccg aat tgt att ata tcc gat aag tac atg gcc tgg acg ggt tat ttt<br>Pro Asn Cys Ile Ile Ser Asp Lys Tyr Met Ala Trp Thr Gly Tyr Asn<br>115                 120                 125                 130 | 441 |
| gcg gat aag tat atg ata cca aga atc atg ttt gat ggg atg agt tgt<br>Ala Asp Lys Tyr Met Ile Pro Arg Ile Met Asn Asp Gly Met Ser Cys<br>            135                 140                 145 | 489 |
| ttt aat gaa tta tgt tac aac aat ttg tac ata tct aag gtg ttt agt<br>Asn Asn Glu Leu Cys Tyr Asn Asn Leu Tyr Ile Ser Lys Val Asn Ser<br>            150                 155                 160 | 537 |
| ggt ttg cca gga tca gaa caa ttt gtt gtt cct ggt ttg cct gat agg<br>Gly Leu Pro Gly Ser Glu Gln Phe Val Val Pro Gly Leu Pro Asp Arg<br>            165                 170                 175 | 585 |
| att gag cta acg agg aac cag ctg cca gat gag ttt aac cca agc tcg<br>Ile Glu Leu Thr Arg Asn Gln Leu Pro Asp Glu Phe Asn Pro Ser Ser<br>180                 185                 190 | 633 |
| att gac aca agt gag ttt cgt cag cgg gct agg gat gcc gag gtg agg<br>Ile Asp Thr Ser Glu Phe Arg Gln Arg Ala Arg Asp Ala Glu Val Arg<br>195                 200                 205                 210 | 681 |
| gct tat gga gtt gtg atc aat agt ttt gag gag ttg gaa caa gaa tat<br>Ala Tyr Gly Val Val Ile Asn Ser Phe Glu Glu Leu Glu Gln Glu Tyr<br>            215                 220                 225 | 729 |
| gtt aat gag tat aaa aag tta aga ggg ggt aag gtt tgg tgc atc ggg<br>Val Asn Glu Tyr Lys Lys Leu Arg Gly Gly Lys Val Trp Cys Ile Gly<br>            230                 235                 240 | 777 |
| cca ttg tca cta tgc aat gac gat gat tcg ggt aaa tcc caa aga gga<br>Pro Leu Ser Leu Cys Asn Asp Asp Asp Ser Gly Lys Ser Gln Arg Gly<br>            245                 250                 255 | 825 |
| aac gca gcc tca atc gat atg gaa cat tgc tta aag tgg ctt gat tca<br>Asn Ala Ala Ser Ile Asp Met Glu His Cys Leu Lys Trp Leu Asp Ser<br>260                 265                 270 | 873 |
| caa gaa ccc aac tct gtg gtt tat gct tgt ttt ggt agt ctt gtt aga<br>Gln Glu Pro Asn Ser Val Val Tyr Ala Cys Phe Gly Ser Leu Val Arg<br>275                 280                 285                 290 | 921 |
| ctt aac act cca caa ctt att gag ctt ggt tta ggg cta gaa gca tca<br>Leu Asn Thr Pro Gln Leu Ile Glu Leu Gly Leu Gly Leu Glu Ala Ser<br>            295                 300                 305 | 969 |
| aat cac ccg ttt att tgg gtt atc aaa tct gtt cac aga gag aag gag<br>Asn His Pro Phe Ile Trp Val Ile Lys Ser Val His Arg Glu Lys Glu<br>            310                 315                 320 | 1017 |
| gtc gaa gag tgg tta gca gaa agt ggt ttc gag gag agg att aaa gat<br>Val Glu Glu Trp Leu Ala Glu Ser Gly Phe Glu Glu Arg Ile Lys Asp<br>            325                 330                 335 | 1065 |
| aga ggg tta ata atc cga ggt tgg gcc cca caa gtg cta atc ttg tct<br>Arg Gly Leu Ile Ile Arg Gly Trp Ala Pro Gln Val Leu Ile Leu Ser<br>340                 345                 350 | 1113 |
| cat cct tcg att gga ggg ttc ttg acg cat tgt gga tgg aat tcg act<br>His Pro Ser Ile Gly Gly Phe Leu Thr His Cys Gly Trp Asn Ser Thr<br>355                 360                 365                 370 | 1161 |
| cta gaa tca gtg tgt gct ggt gtt ccc atg atc acg tgg cct cag ttt<br>Leu Glu Ser Val Cys Ala Gly Val Pro Met Ile Thr Trp Pro Gln Asn<br>            375                 380                 385 | 1209 |
| gcc gag cag ttt att aat gaa aag cta atc gtg caa gtt cta ggc aca<br>Ala Glu Gln Asn Ile Asn Glu Lys Leu Ile Val Gln Val Leu Gly Thr | 1257 |

-continued

```
                390                 395                 400
ggt gtg ggt gtt gga gct gat tct gtt gtt cat gtg ggc gaa gaa gat      1305
Gly Val Gly Val Gly Ala Asp Ser Val Val His Val Gly Glu Glu Asp
            405                 410                 415 atg tcg ggg gtg aaa gtg aca aag gac agt ctc aag aag gct atc gag      1353
Met Ser Gly Val Lys Val Thr Lys Asp Ser Leu Lys Lys Ala Ile Glu
        420                 425                 430 ttg gtc atg gat gaa ggg att gaa gga acc aag aga cga aag aaa gcg      1401
Leu Val Met Asp Glu Gly Ile Glu Gly Thr Lys Arg Arg Lys Lys Ala
435                 440                 445                 450 aaa gag ctt ggc aag ata gca aat aac gca ata aag gag gga ggg tct      1449
Lys Glu Leu Gly Lys Ile Ala Asn Asn Ala Ile Lys Glu Gly Gly Ser
                455                 460                 465 tca ttc ttg aac ttg aca ctg cta att caa gac ata atg tat cat gct      1497
Ser Phe Leu Asn Leu Thr Leu Leu Ile Gln Asp Ile Met Tyr His Ala
            470                 475                 480 aac gca aca agc taaaatccta tatccaaact ttcagttata aaaaaaaaa          1549
Asn Ala Thr Ser
        485 aaaaaaaaaa aaaaaa                                                    1566
```

<210> SEQ ID NO 12
<211> LENGTH: 486
<212> TYPE: PRT
<213> ORGANISM: Senesio cruentus

<400> SEQUENCE: 12

```
Met Ala Ile Asp Lys Leu His Phe Leu Leu Val Pro His Ile Gly Pro
  1               5                  10                  15

Gly His Thr Ile Pro Met Ile Asp Met Ala Lys Leu Leu Ser Lys Gln
             20                  25                  30

Pro Asn Val Ala Met Val Thr Ile Ala Thr Thr Pro Leu Asn Val Ile
         35                  40                  45

Arg Tyr Gly Pro Thr Leu Ala Gly Leu Ile Lys Thr Arg Phe Leu Glu
     50                  55                  60

Leu Pro Asn Pro Ala Ala Glu Val Gly Leu Pro Glu Gly Cys Glu Ser
 65                  70                  75                  80

Thr Asp Lys Leu Pro Ser Leu Asp Asn Val Pro Asn Asn Leu Ala Ala
                 85                  90                  95

Ile Glu Met Leu Gln Gln Lys Leu Glu Glu Arg Asn Gly Thr Leu Asn
            100                 105                 110

Pro Arg Pro Asn Cys Ile Ile Ser Asp Lys Tyr Met Ala Trp Thr Gly
        115                 120                 125

Tyr Asn Ala Asp Lys Tyr Met Ile Pro Arg Ile Met Asn Asp Gly Met
    130                 135                 140

Ser Cys Asn Asn Glu Leu Cys Tyr Asn Leu Tyr Ile Ser Lys Val
145                 150                 155                 160

Asn Ser Gly Leu Pro Gly Ser Glu Gln Asn Val Val Pro Gly Leu Pro
                165                 170                 175

Asp Arg Ile Glu Leu Thr Arg Asn Gln Leu Pro Asp Glu Asn Asn Pro
            180                 185                 190

Ser Ser Ile Asp Thr Ser Glu Asn Arg Gln Arg Ala Arg Asp Ala Glu
        195                 200                 205

Val Arg Ala Tyr Gly Val Val Ile Asn Ser Asn Glu Glu Leu Glu Gln
    210                 215                 220

Glu Tyr Val Asn Glu Tyr Lys Lys Leu Arg Gly Gly Lys Val Trp Cys
```

```
                225                 230                 235                 240
Ile Gly Pro Leu Ser Leu Cys Asn Asp Asp Ser Gly Lys Ser Gln
                245                 250                 255

Arg Gly Asn Ala Ala Ser Ile Asp Met Glu His Cys Leu Lys Trp Leu
            260                 265                 270

Asp Ser Gln Glu Pro Asn Ser Val Val Tyr Ala Cys Asn Gly Ser Leu
        275                 280                 285

Val Arg Leu Asn Thr Pro Gln Leu Ile Glu Leu Gly Leu Gly Leu Glu
    290                 295                 300

Ala Ser Asn His Pro Asn Ile Trp Val Ile Lys Ser Val His Arg Glu
305                 310                 315                 320

Lys Glu Val Glu Glu Trp Leu Ala Glu Ser Gly Phe Glu Glu Arg Ile
                325                 330                 335

Lys Asp Arg Gly Leu Ile Ile Arg Gly Trp Ala Pro Gln Val Leu Ile
            340                 345                 350

Leu Ser His Pro Ser Ile Gly Gly Phe Leu Thr His Cys Gly Trp Asn
        355                 360                 365

Ser Thr Leu Glu Ser Val Cys Ala Gly Val Pro Met Ile Thr Trp Pro
    370                 375                 380

Gln Asn Ala Glu Gln Asn Ile Asn Glu Lys Leu Ile Val Gln Val Leu
385                 390                 395                 400

Gly Thr Gly Val Gly Val Gly Ala Asp Ser Val Val His Val Gly Glu
                405                 410                 415

Glu Asp Met Ser Gly Val Lys Val Thr Lys Asp Ser Leu Lys Lys Ala
            420                 425                 430

Ile Glu Leu Val Met Asp Glu Gly Ile Glu Gly Thr Lys Arg Arg Lys
        435                 440                 445

Lys Ala Lys Glu Leu Gly Lys Ile Ala Asn Asn Ala Ile Lys Glu Gly
    450                 455                 460

Gly Ser Ser Phe Leu Asn Leu Thr Leu Leu Ile Gln Asp Ile Met Tyr
465                 470                 475                 480

His Ala Asn Ala Thr Ser
                485

<210> SEQ ID NO 13
<211> LENGTH: 1688
<212> TYPE: DNA
<213> ORGANISM: Clitoria ternatea
<220> FEATURE:
<221> NAME/KEY: CDS
<222> LOCATION: (73)..(1512)

<400> SEQUENCE: 13
ggcacgagtt tgccttctta taatcttagt ctagttccaa acctaggtaa tattctccaa      60
agaaagatca ag atg ggc gat gaa cac cat act ctg cac atc ttt gtc ttc    111
              Met Gly Asp Glu His His Thr Leu His Ile Phe Val Phe
                1               5                   10 cct ttc tta gct cac ggt cac ttg ata cca acc att gac atg gcc aaa      159
Pro Phe Leu Ala His Gly His Leu Ile Pro Thr Ile Asp Met Ala Lys
    15                  20                  25 tta ttt gct gaa aaa tac gtg aag gtc acc ata att acc aca ccc ctg      207
Leu Phe Ala Glu Lys Tyr Val Lys Val Thr Ile Ile Thr Thr Pro Leu
30                  35                  40                  45 aat gca cct ttc ttc ttc aaa gcc ata gaa aaa acc aaa att tgt tcc      255
Asn Ala Pro Phe Phe Phe Lys Ala Ile Glu Lys Thr Lys Ile Cys Ser
                50                  55                  60
```

-continued

| | |
|---|---|
| aac cgg atc cac atc caa gcc att gag ttt ccc tgc caa gag gct ggt<br>Asn Arg Ile His Ile Gln Ala Ile Glu Phe Pro Cys Gln Glu Ala Gly<br>               65                      70                      75 | 303 |
| tta cct ggt gga tgt gaa aac cta gac tcg gtt cca tcc ttt gat ttc<br>Leu Pro Gly Gly Cys Glu Asn Leu Asp Ser Val Pro Ser Phe Asp Phe<br>          80                      85                      90 | 351 |
| ttc cct tcc ttt ttc aaa gca act agg ttg ctc caa gtg cca ttt gaa<br>Phe Pro Ser Phe Phe Lys Ala Thr Arg Leu Leu Gln Val Pro Phe Glu<br>          95                     100                  105 | 399 |
| caa cta ttg att gag caa cgc ccc aac tgt gtc gtt gct gat att ttc<br>Gln Leu Leu Ile Glu Gln Arg Pro Asn Cys Val Val Ala Asp Ile Phe<br>110                  115                 120               125 | 447 |
| ttc tca tgg gta act gat tcc gct gcc aag ttc gga att cct agg att<br>Phe Ser Trp Val Thr Asp Ser Ala Ala Lys Phe Gly Ile Pro Arg Ile<br>               130                 135               140 | 495 |
| gta ttc tca ggt gtc agt ttt ttc tcc tct tgc gct ctt gag tgc atg<br>Val Phe Ser Gly Val Ser Phe Phe Ser Ser Cys Ala Leu Glu Cys Met<br>             145                 150               155 | 543 |
| aga ctt tac aag tct ttt gag aat gtt tct tct gat tct gaa ccc ttt<br>Arg Leu Tyr Lys Ser Phe Glu Asn Val Ser Ser Asp Ser Glu Pro Phe<br>        160                 165               170 | 591 |
| ctc att cct ggt ctc ccc ggt gag att aaa ctc aca agg gcg caa ttg<br>Leu Ile Pro Gly Leu Pro Gly Glu Ile Lys Leu Thr Arg Ala Gln Leu<br>             175                 180               185 | 639 |
| cca cct cat ctg aaa aat gag gaa aca ccc ttt gca aaa ata att aac<br>Pro Pro His Leu Lys Asn Glu Glu Thr Pro Phe Ala Lys Ile Ile Asn<br>190                  195                 200               205 | 687 |
| gag gca agg gaa gca gag aag aga agc tat ggg gtg ctt att aac agc<br>Glu Ala Arg Glu Ala Glu Lys Arg Ser Tyr Gly Val Leu Ile Asn Ser<br>               210                 215               220 | 735 |
| ttc tat gaa ctg gag aag gat tat gca gat tat tac agg aag gaa cta<br>Phe Tyr Glu Leu Glu Lys Asp Tyr Ala Asp Tyr Tyr Arg Lys Glu Leu<br>             225                 230               235 | 783 |
| gga aga aaa gca tgg cat att ggt cca ttg tcc ctt tgc aat agg gac<br>Gly Arg Lys Ala Trp His Ile Gly Pro Leu Ser Leu Cys Asn Arg Asp<br>        240                 245               250 | 831 |
| ata gga gaa aag gca ctt aga gga aag gaa gca tct ttt gat ggg cat<br>Ile Gly Glu Lys Ala Leu Arg Gly Lys Glu Ala Ser Phe Asp Gly His<br>             255                 260               265 | 879 |
| gag tgc tta aaa tgg ctt gac aca aag gaa ccc aat tca gtt gtt tat<br>Glu Cys Leu Lys Trp Leu Asp Thr Lys Glu Pro Asn Ser Val Val Tyr<br>270                  275                 280               285 | 927 |
| gtg tgc ttt gga agt aca aca aac ttt cct gat tct caa ctt aca gaa<br>Val Cys Phe Gly Ser Thr Thr Asn Phe Pro Asp Ser Gln Leu Thr Glu<br>               290                 295               300 | 975 |
| att gcc aaa ggt ctt gaa gct tca gag cag caa ttc att tgg gtt gtg<br>Ile Ala Lys Gly Leu Glu Ala Ser Glu Gln Gln Phe Ile Trp Val Val<br>             305                 310               315 | 1023 |
| agg aaa agc gag aaa gat gga aaa gac tca gaa gag tgg cta cct gaa<br>Arg Lys Ser Glu Lys Asp Gly Lys Asp Ser Glu Glu Trp Leu Pro Glu<br>        320                 325               330 | 1071 |
| ggg ttt gag aga aag atg gaa ggt aag gga cta att ata aga ggt tgg<br>Gly Phe Glu Arg Lys Met Glu Gly Lys Gly Leu Ile Ile Arg Gly Trp<br>             335                 340               345 | 1119 |
| gcg cca caa gtg ttg att ctt gaa cat gaa gct gtt gga gct ttt gtg<br>Ala Pro Gln Val Leu Ile Leu Glu His Glu Ala Val Gly Ala Phe Val<br>350                  355                 360               365 | 1167 |
| act cat tgt gga tgg aat tca act ttg gaa gcg ata tgt gca ggg gtg<br>Thr His Cys Gly Trp Asn Ser Thr Leu Glu Ala Ile Cys Ala Gly Val<br>               370                 375               380 | 1215 |

-continued

```
tcc ttg gtc acc tgg cct gtt gct gca gag caa ttt tac aat gag aag      1263
Ser Leu Val Thr Trp Pro Val Ala Ala Glu Gln Phe Tyr Asn Glu Lys
        385                 390                 395 ctt ctg act gag gtc ctt gga att ggg gtc cct gtt ggt gct aaa aaa      1311
Leu Leu Thr Glu Val Leu Gly Ile Gly Val Pro Val Gly Ala Lys Lys
            400                 405                 410 tgg ggt atg ttt gag ggc gat agt atc aaa tgg gat gca gtg gag aag      1359
Trp Gly Met Phe Glu Gly Asp Ser Ile Lys Trp Asp Ala Val Glu Lys
    415                 420                 425 gct gtg aag agg ata atg ata ggg gaa gaa gcc aat gaa atg agg aat      1407
Ala Val Lys Arg Ile Met Ile Gly Glu Glu Ala Asn Glu Met Arg Asn
430                 435                 440                 445 aaa gtg aag ctg ctt tca caa ctg gct agg agg gcc gtg gaa gaa ggg      1455
Lys Val Lys Leu Leu Ser Gln Leu Ala Arg Arg Ala Val Glu Glu Gly
                450                 455                 460 gga tcg tct gac tcg gat ttg aat gct ttc att gag gag ttg aga tcc      1503
Gly Ser Ser Asp Ser Asp Leu Asn Ala Phe Ile Glu Glu Leu Arg Ser
    465                 470                 475 atg agt cac tgataattca caaaaatatg ctgcatatgt tatgttctt              1552
Met Ser His
        480 tccttcaaaa gattggaaaa tgtaatttgt ttgctgggat tcattctgtt tgatgtagca    1612 atgaagtagc atgatgaatt tgtctgactg tttaataaag ttttaagaa gtttatgaaa    1672 aaaaaaaaaa aaaaaa                                                    1688
```

<210> SEQ ID NO 14
<211> LENGTH: 480
<212> TYPE: PRT
<213> ORGANISM: Clitoria ternatea

<400> SEQUENCE: 14

```
Met Gly Asp Glu His His Thr Leu His Ile Phe Val Phe Pro Phe Leu
  1               5                  10                  15

Ala His Gly His Leu Ile Pro Thr Ile Asp Met Ala Lys Leu Phe Ala
             20                  25                  30

Glu Lys Tyr Val Lys Val Thr Ile Ile Thr Thr Pro Leu Asn Ala Pro
         35                  40                  45

Phe Phe Phe Lys Ala Ile Glu Lys Thr Lys Ile Cys Ser Asn Arg Ile
     50                  55                  60

His Ile Gln Ala Ile Glu Phe Pro Cys Gln Glu Ala Gly Leu Pro Gly
 65                  70                  75                  80

Gly Cys Glu Asn Leu Asp Ser Val Pro Ser Phe Asp Phe Pro Ser
                 85                  90                  95

Phe Phe Lys Ala Thr Arg Leu Leu Gln Val Pro Phe Glu Gln Leu Leu
            100                 105                 110

Ile Glu Gln Arg Pro Asn Cys Val Val Ala Asp Ile Phe Phe Ser Trp
        115                 120                 125

Val Thr Asp Ser Ala Ala Lys Phe Gly Ile Pro Arg Ile Val Phe Ser
130                 135                 140

Gly Val Ser Phe Phe Ser Ser Cys Ala Leu Glu Cys Met Arg Leu Tyr
145                 150                 155                 160

Lys Ser Phe Glu Asn Val Ser Ser Asp Ser Gly Pro Phe Leu Ile Pro
                165                 170                 175

Gly Leu Pro Gly Glu Ile Lys Leu Thr Arg Ala Gln Leu Pro Pro His
            180                 185                 190
```

-continued

```
Leu Lys Asn Glu Glu Thr Pro Phe Ala Lys Ile Ile Asn Glu Ala Arg
    195                 200                 205

Glu Ala Glu Lys Arg Ser Tyr Gly Val Leu Ile Asn Ser Phe Tyr Glu
    210                 215                 220

Leu Glu Lys Asp Tyr Ala Asp Tyr Tyr Arg Lys Glu Leu Gly Arg Lys
225                 230                 235                 240

Ala Trp His Ile Gly Pro Leu Ser Leu Cys Asn Arg Asp Ile Gly Glu
                245                 250                 255

Lys Ala Leu Arg Gly Lys Glu Ala Ser Phe Asp Gly His Glu Cys Leu
            260                 265                 270

Lys Trp Leu Asp Thr Lys Glu Pro Asn Ser Val Val Tyr Val Cys Phe
        275                 280                 285

Gly Ser Thr Thr Asn Phe Pro Asp Ser Gln Leu Thr Glu Ile Ala Lys
    290                 295                 300

Gly Leu Glu Ala Ser Glu Gln Gln Phe Ile Trp Val Val Arg Lys Ser
305                 310                 315                 320

Glu Lys Asp Gly Lys Asp Ser Glu Glu Trp Leu Pro Glu Gly Phe Glu
                325                 330                 335

Arg Lys Met Glu Gly Lys Gly Leu Ile Ile Arg Gly Trp Ala Pro Gln
            340                 345                 350

Val Leu Ile Leu Glu His Glu Ala Val Gly Ala Phe Val Thr His Cys
        355                 360                 365

Gly Trp Asn Ser Thr Leu Glu Ala Ile Cys Ala Gly Val Ser Leu Val
    370                 375                 380

Thr Trp Pro Val Ala Ala Glu Gln Phe Tyr Asn Glu Lys Leu Leu Thr
385                 390                 395                 400

Glu Val Leu Gly Ile Gly Val Pro Val Gly Ala Lys Lys Trp Gly Met
                405                 410                 415

Phe Glu Gly Asp Ser Ile Lys Trp Asp Ala Val Glu Lys Ala Val Lys
            420                 425                 430

Arg Ile Met Ile Gly Glu Glu Ala Asn Glu Met Arg Asn Lys Val Lys
        435                 440                 445

Leu Leu Ser Gln Leu Ala Arg Arg Ala Val Glu Glu Gly Gly Ser Ser
    450                 455                 460

Asp Ser Asp Leu Asn Ala Phe Ile Glu Glu Leu Arg Ser Met Ser His
465                 470                 475                 480
```